US00PP35892P2

(12) United States Plant Patent
Meilland

(10) Patent No.: US PP35,892 P2
(45) Date of Patent: Jul. 2, 2024

(54) HYBRID TEA ROSE PLANT NAMED 'MEIPAPEY'

(50) Latin Name: *Rosa hybrida*
Varietal Denomination: MEIPAPEY

(71) Applicant: The Conard Pyle Company, West Grove, PA (US)

(72) Inventor: Alain Antoine Meilland, Antibes (FR)

(73) Assignee: The Conard Pyle Company, West Grove, PA (US)

( * ) Notice: Subject to any disclaimer, the term of this patent is extended or adjusted under 35 U.S.C. 154(b) by 0 days.

(21) Appl. No.: 18/233,000

(22) Filed: Aug. 11, 2023

(51) Int. Cl.
*A01H 5/02* (2018.01)
*A01H 6/74* (2018.01)

(52) U.S. Cl.
USPC ..... Plt./137

(58) Field of Classification Search
USPC ..... Plt./101, 130, 137
See application file for complete search history.

(56) References Cited

U.S. PATENT DOCUMENTS

PP28,659 P3 11/2017 Meilland

*Primary Examiner* — Susan McCormick Ewoldt
*Assistant Examiner* — Zachariah Allan Kay
(74) *Attorney, Agent, or Firm* — Panitch Schwarze Belisario & Nadel LLI; Stephany G. Small; Travis W. Bliss

(57) ABSTRACT

A new and distinct variety of hybrid tea rose plant, referred to by its cultivar name, 'MEIPAPEY', is disclosed. The new variety forms full, pink colored flowers. Dense, semi-glossy foliage is formed, which contrasts with the blossoms. A shrub growth habit is displayed. The new variety is well suited for providing attractive ornamentation in the landscape.

1 Drawing Sheet

Latin name of genus and species of plant claimed: *Rosa hybrida.*

Variety denomination: 'MEIPAPEY'.

STATEMENT REGARDING PRIOR DISCLOSURES BY THE INVENTOR

The first offer for sale of the new variety was Oct. 28, 2022, in the United States of America. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was the 'TAN99176' variety (not patented). The male parent (i.e., the pollen parent) of the new variety was the 'ADAHUIN' variety (not patented).

The parentage of the new variety can be summarized as follows:

'TAN99176' X 'ADAHUIN'

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, semi-hardwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) displays a pink colored flower
(b) produces full flowers, and
(c) emits a strong fragrance.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'TAN99176' variety (i.e., the seed parent) exhibits a climbing growth habit, whereas the new variety exhibits a shrub growth habit. In addition, the 'ADAHUIN' variety (i.e., pollen parent) produces red colored flowers, whereas the new variety produces pink colored flowers. Moreover, the new variety can be readily distinguished from other similar non-parental varieties. For example, the 'MEINOSTAIR' variety (U.S. Plant Pat. No. 28,659) provides apricot-colored flowers which have approximately 48 petals on average, whereas the new variety produces pink colored flowers which typically have between 120 to 130 petals.

The new variety has been named 'MEIPAPEY'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately three years of age and were observed during May while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms and The R.H.S. Colour Chart designation used herein represents the closest color observed on the majority of the specified botanical feature. The description is based on the observation of three-years-old specimens of the new variety during May while budded on their own roots and growing outdoors at Le Cannet des Maures, Var, France.

Botanical classification: *Rosa hybrida* cultivar MEIPAPEY.

Commercial classification: Hybrid Tea Rose Plant.

Plant:

*Habit*.—Shrub.

*Height*.—Approximately 100 cm on average.

*Width*.—Approximately 90 cm on average.

Branches:

*Color*.—Young stems: Yellow-Green Group 144A. — adult wood: a color between Yellow-Green Group 144A and Yellow-Green Group 146A.

*Length*.—From the crown to the flower is typically between 50 cm to 80 cm.

*Diameter*.—Approximately 0.6 cm on average.

*Prickles*.—Configuration on adult stems: concave and elongated, few curved downwards on the upper surface and concave on the under surface. — long prickles — quantity: typically between 1 to 3 prickles on average per 10 cm long young stem and typically between 1 to 5 prickles on average per 10 cm long adult stem. — long prickles — length: typically between 0.3 cm to 0.5 cm on young stems and typically between 0.5 cm to 0.7 cm on adult stems. — long prickles — width at base: approximately 0.1 cm on average on young stems and typically between 0.1 cm to 0.2 cm on adult stems. — long prickles — base shape: elliptical, long, and very narrow on young stems and on adult stems. — long prickles — color on young stems: a color between Yellow-Green Group 150C and Yellow-Green Group 151C. — long prickles — color on adult stems: a color between Yellow-Green Group 150C and Yellow-Green Group 151C. — small prickles: absent.

*Internode*.—Numbers on the entire branch: approximately 15 on average. — length: typically between 2.5 cm to 6.0 cm.

Foliage:

*General appearance*.—Dense, semi-glossy.

*Number of leaflets*.—3, 5, 7; most often 5.

5 *leaflets leaf*.—Length: approximately 14.0 cm on average. — width: approximately 10.0 cm on average.

*Terminal leaflet*.—Length: approximately 5.7 cm on average. — width: typically between 2.5 cm to 4.0 cm.

*Young shoots*.—Anthocyanin coloration: Greyed-Purple Group 187A.

*New foliage*.—Upper surface color: a color between Yellow-Green Group 146A and Yellow-Green Group 147A, more or less suffused with Greyed-Purple Group 187A. — under surface color: Yellow-Green Group 146B more or less suffused with Greyed-Purple Group 187A.

*Adult foliage*.—Upper surface color: a color between Yellow-Green Group 147A and Green Group 139A. — under surface color: a color between Yellow-Green Group 147A and 147B.

Leaflets:

*Shape*.—Tip: acuminate. — base: obtuse.

*Intensity of glossiness*.—Medium.

*Texture*.—Moderately leathery.

*Smoothness*.—Upper surface is smooth; under surface is bumpy.

*General appearance*.—Oval.

*Serration*.—Small and single.

*Undulation on the margin*.—Strong.

*Venation*.—Color is Yellow-Green Group 147A and pattern is imparipinnate.

*Petiole rachis*.—Color of upper surface: Yellow-Green Group 144A more or less bordered with Green Group 141A. — color of under surface: Yellow-Green Group 144A. — texture: upper surface is glandular, under surface is few prickles. — rachis of terminal leaflet: length is typically between 4.0 cm to 5.0 cm and diameter is approximately 0.1 cm on average.

*Petioles*.—Upper surface: glandular. — under surface: glandular. — color of upper surface: Yellow-Green Group 144A more or less bordered with Green Group 141A. — color of under surface: Yellow-Green Group 144A. — length: typically between 3.0 cm to 4.0 cm. — diameter: approximately 0.1 cm on average.

*Stipules*.—Length: approximately 1.5 cm on average. — width: approximately 0.5 cm on average. — general appearance: rather broad. — texture: upper surface is smooth; under surface is smooth and very glandular on the edge. — color of upper surface: Green Group 141A on the edge and Yellow-Green Group 144A towards the center. — color of under surface: Green Group 143A.

Inflorescence:

*Number of flowers per stem*.—Typically between 1 to 5 flowers per stem.

*Lastingness of the bloom*.—On the plant: approximately 7 days on average. — in vase: not tested.

*Bud*.—Shape: ovoid. — size: medium. — length: approximately 4.0 cm on average. — width: approximately 2.5 cm on average. — color as calyx breaks: upper surface: Red-Purple Group 62D amply suffused with Red-Purple Group 57C on the edge of the petal; basal spot is very little and color is Yellow Group 5B. under surface: Red-Purple Group 62C amply suffused with Red-Purple Group 57C; basal spot is very little and color is Yellow Group 5C.

*Sepals*.—Number: commonly 5. — length: typically between 3.0 cm to 4.0 cm. — width: typically between 1.0 cm to 1.5 cm (on median part). — shape: at the top: elongate and narrow. at the base: flat at union with the receptacle. — extensions: typically 2 sepals without extensions and 3 sepals with medium extension. — upper surface: texture: tomentous. color: Yellow-Green Group 144A more or less suffused with Green Group 143A and covered with many hairs Green-White Group 157A. — under surface: texture: tomentous. color: Yellow-Green Group 144A more or less suffused with Green Group 143A.

*Receptacle*.—Color: Yellow-Green Group 144A. — length: typically between 1.0 cm to 1.5 cm. — width: typically between 1.0 cm to 1.5 cm. — surface: smooth. — shape: funnel shaped.

*Peduncle*.—Length: typically between 4.5 cm to 6.0 cm. — width: approximately 0.4 cm on average. — surface: very slightly glandular. — color: a color between Yellow-Green Group 144A and Yellow-Green Group 146A.

*Flower*.—Diameter when open: approximately 8.0 cm on average. — depth of the flower: approximately 4.0 cm on average. — shape: cup shaped. — shape when viewed from above: rounded. — shape of the upper part of the flower profile: concave. — shape of the lower part of the flower profile: flat. — type: full. — number of petals under normal conditions: typically between 120 to 130. — petals: general shape: external petals are rounded; internal petals are obovate narrow. shape at the base: external petals are rounded; internal petals are attenuated. shape at the top: rounded. texture: semi-hard. length: external petals are typically between 4.0 cm to 5.0 cm; internal petals are typically between 2.0 cm to 3.0 cm. width: external petals are typically between 3.5 cm to 6.0 cm; internal petals are typically between 1.5 cm to 2.5 cm. — undulation of the petal: strong. — reflexing of the petal: absent. — petal incision: weak. — petal arrangement: imbricated without petaloids. — petal drop: petals drop off cleanly before drying. — fragrance: strong (lychees and grapefruit). — discoloration of the flower: no. — color when opening: basal spot on the upper surface: Yellow Group 5B. upper surface external petals: Red Group 36D amply suffused with Red-Purple Group 62B at the edge of the petal. upper surface internal petals: Red-Purple Group 62C amply suffused with Red-Purple Group 57C at the edge of the petal. basal spot on the under surface: Yellow Group 5C. under surface external petals: Red-Purple Group 62D amply suffused with Red-Purple Group 62B. under surface internal petals: Red-Purple Group 62C amply suffused with Red-Purple Group 57C. — color of the open flower: basal spot on upper surface: Yellow Group 5D. upper surface external petals: Red Group 36D slightly suffused with Red-Purple Group 62B towards the edge of the petal. upper surface internal petals: Red-Purple Group 62C slightly suffused with Red-Purple Group 62A toward the edge of the petal. basal spot on under surface: Yellow Group 5D. under surface external petals: Red Group 36D amply suffused with Red-Purple Group 62C. under surface internal petals: Red-Purple Group 62C amply suffused with Red-Purple Group 62A. — anthers: typically between 85 to 95, length is approximately 0.2 cm on average, width is approximately 0.1 cm on average, coloration is Yellow Group 13A, and arrangement is regular around styles. — filaments: length is approximately 0.5 cm on average and coloration is Yellow Group 13C. — styles: length is typically between 0.4 cm to 1.0 cm, coloration is Green-White Group 157A at the base and Red-Purple Group 57B near the stigmas, and number is typically between 80 to 90. — stigmas: length is typically less than 0.1 cm on average and coloration is Yellow-Orange Group 19A. — pollen: medium quantity; color is Yellow-Orange Group 22A. — hips: information not available.

Development:

*Vegetation*.—Strong.

*Blooming*.—Early in the season, abundant and recurrent, typically from May to first frost in France.

*USDA hardiness zone*.—Tested to Zone 5.

*Tolerance to disease*.—Good, and particularly against rust (*Phragmidium* sp.) and downy mildew (*Peronospora sparsa*).

The new 'MEIPAPEY' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEI-PAPEY' characterized by the following combination of characteristics:

(a) displays a pink colored flower, (b) produces full flowers, and (c) emits a strong fragrance;

substantially as herein shown and described.

* * * * *

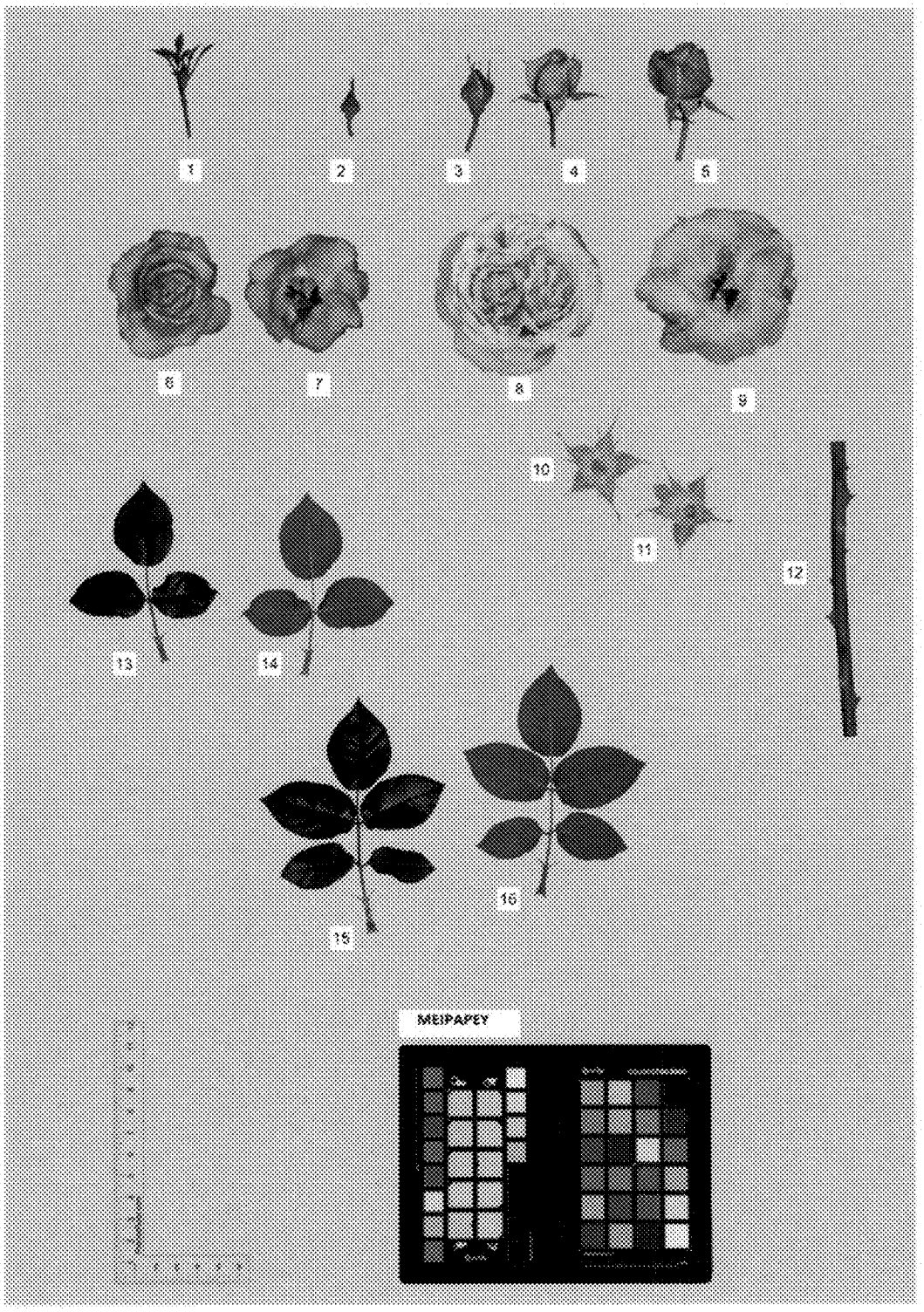
1
2
3
4
5
6
7
8
9
10
11
12
13
14
15
16
MEIPAPEY